United States Patent

Chin

[11] 4,390,549
[45] Jun. 28, 1983

[54] N-TETRACHLOROETHYLTHIO BENZOYL ANILIDES USEFUL AS ACARICIDES AND TO CONTROL MOSQUITOES

[75] Inventor: Hsiao-Ling M. Chin, Walnut Creek, Calif.

[73] Assignee: Stauffer Chemical Company, Westport, Conn.

[21] Appl. No.: 277,355

[22] Filed: Jun. 25, 1981

[51] Int. Cl.³ .................... A01N 37/00; A01N 37/18
[52] U.S. Cl. .................................... 424/324; 424/298
[58] Field of Search ............................... 424/324, 298

[56] References Cited

U.S. PATENT DOCUMENTS

| | | | |
|---|---|---|---|
| 3,178,447 | 4/1965 | Kohn | 260/309.5 |
| 3,344,153 | 9/1967 | Kuhle et al. | 260/347.2 |
| 3,700,778 | 10/1972 | Hyndman | 424/324 |
| 4,097,512 | 6/1978 | Lam et al. | 424/298 |
| 4,115,582 | 9/1978 | Lam et al. | 424/298 |
| 4,357,346 | 11/1982 | Chin | 424/298 |

FOREIGN PATENT DOCUMENTS 343097 5/1978 Austria.

*Primary Examiner*—Jerome D. Goldberg
*Assistant Examiner*—Freda L. Abramson
*Attorney, Agent, or Firm*—Edwin H. Baker

[57] ABSTRACT

N-tetrachloroethylthio benzoyl anilide compounds having the formula

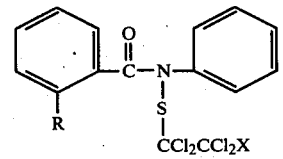

in which R is chlorine, hydrogen, or trifluoromethyl and X is hydrogen or fluorine, useful as acaricides and to control mosquitoes.

5 Claims, No Drawings

N-TETRACHLOROETHYLTHIO BENZOYL ANILIDES USEFUL AS ACARICIDES AND TO CONTROL MOSQUITOES

BACKGROUND OF THE INVENTION

This invention relates to certain novel N-tetrachloroethylthiobenzoyl anilides which are useful as acaricides and to control mosquitoes.

The compounds useful in the practice of the present invention correspond to the formula

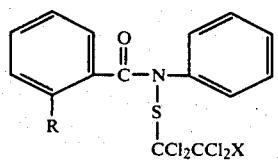

in which R is chlorine, hydrogen, or trifluoromethyl and X is hydrogen or fluorine.

The compounds useful in the practice of this invention are known and have been disclosed in U.S. Pat. Nos. 4,097,512, 4,115,582, and Australian Pat. No. 491,671. The compounds disclosed therein are described as being useful as fungicides except for compound N-1,1,2,2-tetrachloro-2-fluoroethylthio benzanilide (Compound No. 4 herein), which is stated to be useful as a fungicide and an acaricide.

DETAILED DESCRIPTION OF THE INVENTION

The benzanilide compounds useful in the practice of this invention can be prepared according to the following general reaction scheme.

Reaction No. 1

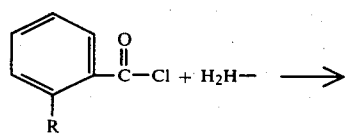

wherein R is as defined.

Generally, a mole amount of the substituted or unsubstituted benzoyl chloride reactant, dissolved in benzene, is added to a mixture of the aniline reactant and a slight mole excess of an HCl acceptor such as triethylamine. The mixture is refluxed for ½ hour and then cooled. The solid reaction product is diluted with a solvent such as ethyl acetate or chloroform and washed with water twice and salt solution once. The final product is dried over MgSO4, filtered and evaporated.

Reaction No. 2

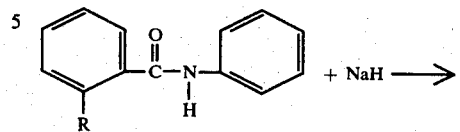

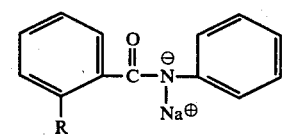

wherein R is as defined.

Under a dry nitrogen atmosphere a mole amount of the reaction product from Reaction No. 1 is dissolved in dry THF. Next, a slight mole excess of NaH is added with stirring. The mixture is refluxed for 1 hour and cooled.

Reaction No. 3

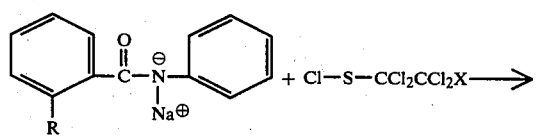

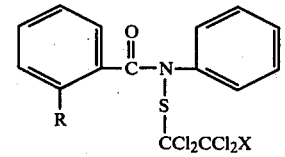

wherein R and X are as defined.

A mole amount of ClSCCl2CCl2X in THF is added dropwise to the reaction mixture of Reaction No. 2. The mixture is refluxed for 2.5 hours and large amount of CH2Cl2 is added to the solid.

The product is washed twice with water, dried over MgSO4 and evaporated.

Preparation of compounds of this invention is illustrated by the following examples.

EXAMPLE I

Preparation of 2-chlorobenzoyl anilide

Fourth and seven-tenths grams (4.7 g) (0.05 mole) anilide and 5.10 g triethylamine are mixed in 150 milliliters (ml) of benzene by stirring. A solution of 8.75 g (0.05 mole) 2-chlorobenzoyl chloride in 50 ml chloroform is added to the first mixture through a dropping funnel. An exothermic reaction takes place. After the addition is finished, the mixture is refluxed for ½ hour. The mixture is cooled with the product solidifying. The product is filtered, added to water, and stirred to dissolve triethylamine hydrochloride. The product is filtered again and dried to yield 11.3 g of the desired product (98% yield) m.p. 115°–117° C.

EXAMPLE II

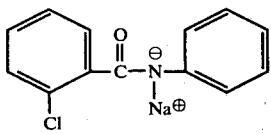

One g (0.003 mole) of the amide reaction product of Example I is dissolved in 40 ml of dry THF under a dry nitrogen atmosphere. Next, 0.12 g (0.005 mole) NaH is added to the mixture with stirring. The mixture is refluxed for one hour and then cooled.

EXAMPLE III

N-1,1,2,2-tetrachloro-2-fluoroethylthio benzanilide

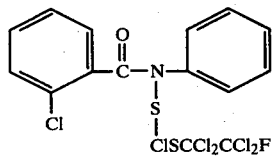

One and four-tenths g (0.0043 mole) of $ClSCCl_2CCl_2F$ dissolved in 10 ml THF is added dropwise to the cooled reaction mixture of Example II. The mixture is then refluxed for 2.5 hours. Next, 150 ml $CH_2Cl_2$ is added, the mixture washed twice with water, dried over $MgSO_4$ and evaporated to yield 2.0 g of the desired product, $n_D^{30} = 1.5940$.

The following is a table of certain selected compounds that are preparable according to the procedure described hereto. Compound numbers are assigned to each compound and are used throughout the remainder of the application.

TABLE I

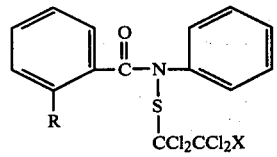

| Compound Number | R | X |
|---|---|---|
| 1 | CF$_3$ | F |
| 2 | H | H |
| 3 | Cl | F |
| 4 | H | F |
| 5 | CF$_3$ | H |

Acaricidal Evaluation Test

The two-spotted mite (2SM), *Tetranychus urticae* (Koch), is employed in tests for miticides. The test procedure is as follows:

Pinto bean plants (Phaseolus sp.) approximately 10 cm tall, are transplanted into sandy loam soil in three-inch clay pots and thoroughly infested with two-spotted mites of mixed ages and sexes. Twenty-four hours later, the infested plants are inverted and dipped for two-three seconds in 50—50 acetone-water solution of the test chemical. Treated plants are held in the greenhouse, and seven days later mortality is determined for both the adult mites and the nymphs hatching from eggs which were on the plants at the time of treatment. Test concentrations range from 0.05% down to that at which 50% mortality occurs. LD$_{50}$ values are expressed below in Table II under the headings "2SM-PE" (i.e., post-embryonic) and "2SM-Eggs," in terms of percent concentration of the test compound in the solution.

Mosquito Evaluation Test

Southern house mosquito larvae (*Culex pipiens quinquefasciatus* Say): Insecticidal activity was determined using third instar larvae of the mosquito *Culex pipiens quinquefasciatus*. Ten larvae were placed in a six ounce paper cup containing 100 milliliters of an aqueous solution of the test chemical. The treated larvae were stored at 70° F. and 48 hours later the mortality was recorded. Test concentrations ranged from one ppm down to that at which approximately 50% mortality occurred. LD$_{50}$ values are expressed below in Table II under the heading "MOS" in terms of ppm of the test compound in the solution.

TABLE II

| Compound Number | 2SM-PE (%) | 2SM-Eggs (%) | MOS (ppm) |
|---|---|---|---|
| 1 | 0.025 | 0.008 | 0.2 |
| 2 | 0.008 | 0.008 | 0.3 |
| 3 | 0.003 | 0.008 | 0.1 |
| 4 | 0.003 | 0.010 | 1.0 |
| 5 | 0.003 | 0.030 | 1.0 |

The compounds of this invention are generally embodied into a form suitable for convenient application. For example, the compound can be embodied into a pesticidal composition which is provided in the form of emulsions, suspensions, solutions, dusts and aerosol sprays. In general, such compositions will contain, in addition to the active compound, the adjuvants which are found normally in pesticide preparations. In these compositions, the active compound of this invention can be employed as the sole pesticide component or it can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite, diatomite; gypsum; clays, propellants, such as dichlorodifluoromethane, etc. If desired, however, the active compound can be applied directly to feedstuffs, seeds, etc., upon which the pests feed. When applied in such a manner, it will be advantageous to use a compound which is not volatile. In connection with the activity of the presently disclosed pesticidal compound, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition, for example, an emulsion, suspension, or aerosol spray. While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.1 to 1.0% by weight of the active pesticide compound.

I claim:

1. A method of killing misquitoes comprising applying thereto an insecticidally effective amount of a compound having the formula

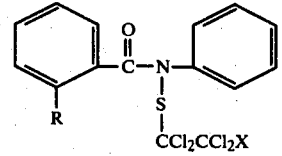

in which R is chlorine, hydrogen, or trifluoromethyl and X is hydrogen or fluorine.

2. The method of claim 1 wherein R is chlorine and X is fluorine.
3. The method of claim 1 wherein R is trifluoromethyl and X is fluorine.
4. The method of claim 1 wherein R is hydrogen and X is hydrogen.
5. The method of claim 1 wherein R is hydrogen and X is fluorine.